US008288593B2

(12) United States Patent
Rauls et al.

(10) Patent No.: US 8,288,593 B2
(45) Date of Patent: Oct. 16, 2012

(54) MENTHOL FLAKES AND METHOD FOR PRODUCING THE SAME

(75) Inventors: Matthias Rauls, Blieskastel (DE); Robert Bayer, Sinsheim (DE); Gunnar Heydrich, Limburgerhof (DE); Lars Frye, Langenfeld (DE); Thomas Wisniewski, Bensheim (DE)

(73) Assignee: BASF SE, Ludwigshafen (DE)

( * ) Notice: Subject to any disclaimer, the term of this patent is extended or adjusted under 35 U.S.C. 154(b) by 234 days.

(21) Appl. No.: 12/664,253

(22) PCT Filed: Jun. 9, 2008

(86) PCT No.: PCT/EP2008/057133
§ 371 (c)(1),
(2), (4) Date: Dec. 11, 2009

(87) PCT Pub. No.: WO2008/152009
PCT Pub. Date: Dec. 18, 2008

(65) Prior Publication Data
US 2010/0185024 A1 Jul. 22, 2010

(30) Foreign Application Priority Data
Jun. 12, 2007 (EP) .................................... 07110117

(51) Int. Cl.
C07C 35/12 (2006.01)
(52) U.S. Cl. ...................................................... 568/829
(58) Field of Classification Search .................... 568/829
See application file for complete search history.

(56) References Cited

U.S. PATENT DOCUMENTS

| 3,023,253 | A | 2/1962 | Bain et al. |
| 3,064,311 | A | 11/1962 | Bain et al. |
| 3,218,361 | A | 11/1965 | Webb |
| 3,739,035 | A | 6/1973 | Webb et al. |
| 5,663,460 | A | 9/1997 | Yamamoto et al. |
| 5,814,231 | A | 9/1998 | Borho et al. |
| 5,914,012 | A | 6/1999 | Kaibel et al. |
| 6,774,269 | B2 | 8/2004 | Iwata et al. |
| 2005/0169987 | A1 | 8/2005 | Korber |
| 2008/0139852 | A1 | 6/2008 | Bergner et al. |
| 2008/0167504 | A1 | 7/2008 | Friedrich et al. |
| 2008/0207957 | A1 | 8/2008 | Friedrich et al. |
| 2008/0214877 | A1 | 9/2008 | Rauls et al. |
| 2010/0010253 | A1 | 1/2010 | Heydrich et al. |
| 2010/0016642 | A1 | 1/2010 | Heydrich et al. |
| 2010/0185024 | A1 | 7/2010 | Rauls et al. |

FOREIGN PATENT DOCUMENTS

| CH | 350461 | A | 1/1961 |
| DE | 2530481 | A1 | 1/1977 |
| DE | 2534558 | A1 | 2/1977 |
| DE | 3302525 | A1 | 7/1984 |
| DE | 19536827 | A1 | 4/1997 |
| DE | 10224087 | A1 | 12/2003 |
| EP | 0804951 | A2 | 11/1997 |
| EP | 1053974 | A1 | 11/2000 |
| EP | 1225163 | A2 | 7/2002 |
| FR | 1374732 | | 10/1964 |
| JP | 2004121903 | A | 4/2004 |
| WO | WO-03/083028 | A2 | 10/2003 |
| WO | WO-2006/056435 | A1 | 6/2006 |
| WO | WO-2006/069659 | A1 | 7/2006 |
| WO | WO-2006/092433 | A1 | 9/2006 |
| WO | WO-2007/023109 | A1 | 3/2007 |
| WO | WO-2008/025851 | A1 | 3/2008 |
| WO | WO-2008/025852 | A1 | 6/2008 |

OTHER PUBLICATIONS

Kuhnert-Brandstaetter, et al. "Thermoanalytische Untersuchungen an Mentholen", Archiv der Pharmazie, vol. 307, No. 7, pp. 497-503 (Jul. 1974).
Bernstein J., "Polymorphism in Molecular Crystals". Oxford, Clarendon Press, pp. 94-150 (2002).
Van't Land, "Industrial Crystallization of Melts", Marcel Dekker, pp. 61-63 (2005).
Arkenbout, "Melt Crystallization Technology", Technomic Publishing Company, Inc., Lancaster, Basel, pp. 229-232 (1995).
Van't Land, C., M. Industrial Crystallization of Melts. Marcel Dekker, 2005, pp. 45-63.
The Sandvik Group, "Sandvik—Your Partners in Melt Granulation Systems", pp. 1-24 (2007).
Die Sandvik-Gruppe, "Sandvik—Ihr partner in der Schmelzengranulierung", pp. 1-24 (2007).
Wynn, Nicholas P., "Separate Organics by Melt Crystallization", Chemical Engineering Process, vol. 88, No. 3, (1992), pp. 52-60.
Wright, Fred, E., "The crystallization of menthol", J. Am. Chem. Soc., vol. 39, No. 8, pp. 1515-1525 (1917).
Kuhnert-Brandstaetter, et al. "Thermoanalytische Untersuchungen an Mentholen", Archiv der Pharmazie, vol. 307, No. 7, pp. 497-503 (1974).
Bernstein J., "Polymorphism in Molecular Crystals", Oxford, Clarendon Press, 2002, pp. 94-150 (2002).
Van't Land, C., M., "Industrial Crystallization of Melts", Marcel Dekker, pp. 61-63 (2005).
Arkenbout, G., F., "Melt Crystallization Technology", Technomic Publishing Company, Inc., Lancaster, Basel, pp. 229-232 (1995).
Third Party Correspondence dated Aug. 31, 2011.

*Primary Examiner* — Brian J Davis
(74) *Attorney, Agent, or Firm* — Connolly Bove Lodge & Hutz LLP

(57) ABSTRACT

The present invention relates to a method for preparing L-menthol in solid form, specifically in the form of flakes, by bringing an L-menthol melt into contact with two chilled surfaces distanced from one another. Moreover, the present invention relates to the L-menthol in solid form obtainable by said method, and also to its use for incorporation into utility and consumer goods of all kinds.

15 Claims, No Drawings

MENTHOL FLAKES AND METHOD FOR PRODUCING THE SAME

This application is a national stage application (under 35 U.S.C. §371) of PCT/EP2008/057133, filed Jun. 9, 2008, which claims benefit of European Application No. 07110117.4, filed Jun. 12, 2007.

The present invention relates to a method for preparing L-menthol in solid form, specifically in the form of flakes, by bringing an L-menthol melt into contact with two chilled surfaces distanced from one another. Moreover, the present invention relates to the L-menthol in solid form obtainable by said method, and also to its use for incorporation into utility and consumer goods of all kinds.

Menthol is a naturally occurring active ingredient which is used widely in pharmacy, cosmetics and the food industry. In natural sources, for example peppermint oil, menthol occurs in the form of four diastereomeric enantiomer pairs, of which only the main component, the (−)-menthol or L-menthol has the desired gustatory and other sensory properties.

For a long time it has been known that L-menthol can solidify in four different crystalline modifications which, for the same chemical composition, have different physical properties, as already described in J. Am. Chem. Soc., Vol. 39 (8), 1917, pp. 1515 to 1525. Thus, in particular the melting points of these different modifications lie between 33° C. and 43° C. as described in Archiv der Pharmazie, 307 (7), 1974, pp. 497 to 503. The melting point of the stable alpha-modification is accordingly 42 to 43° C.

On account of this position of the melting points, L-menthol can be supplied to the end consumer either as a melt kept liquid in heated containers, or else in the form of crystals or other solidified moldings. Generally, all solids which, like L-menthol, have a melting point that is only just above the ambient temperature, have a high tendency to cake and to agglomerate. However, the processing of such caked material is associated with considerable undesired additional expenditure. Should then pure L-menthol, i.e. menthol not treated with auxiliaries, such as, for example release agents, be sold as solid, it must be ensured, either by virtue of a closed cooling chain or by virtue of the type of molding, that the product reaches the end consumer in a pourable form.

Commercially, menthol is available in the form of large crystals which, for a length of 0.5 to 3 cm, have a thickness of from 1 to 3 mm. They are traditionally cultivated in small amounts from naturally obtained peppermint oil by crystallizing the oil in troughs or vats over many days in cooling houses. These crystals have good pourability only in the case of a small bed height, but cake appreciably under increased load and/or at elevated temperature. The technical expenditure for the crystallization, separation and purification of the crystals and the low space-time yield of such a lengthy process make it unattractive for industrial application.

DE 25 30 481 relates to a device for crystallizing substances, in particular optically active menthols, which form coarse needle-shaped and bar-shaped crystals under crystallization conditions. The crystallization method to be conducted discontinuously is carried out using a particular stirrer which prevents the caking of the crystals in the crystal suspension. Finally, the product of value is isolated by means of a centrifuge and dried in a drier.

U.S. Pat. No. 3,023,253 and U.S. Pat. No. 3,064,311 describe flaked L-menthol and a method of producing such flakes by applying a melt of L-menthol to a chilled immersion roller. If desired, the menthol melt can be introduced between a pair of oppositely rotating chilled rollers. The menthol film crystallized on the immersion roller is aftertreated by heat-treating it by introducing heat and strengthening it by applying additional menthol. Both aftertreatments are achieved simultaneously using an application roller. The flakes obtained in this way initially have a good pourability. However, after prolonged storage slight caking occurs which makes mechanical loosening by shaking the container necessary. It is noted that this caking is caused by an albeit mentioned, but not further characterized porous surface and the considerable sublimation of the product associated therewith and that the product obtained in this way can be further processed to give pellets by compaction.

The principle of further coarsening of the primary particles by compaction is also described in DE 102 24 087 relating to compacted menthol in the form of menthol compacts, and a method for the production thereof. However, emphasis is not placed here on the effect of the particle size alone, but on the fact that the primary particles have to be present in a specific crystal modification. By compressing crystals which have been obtained from a solution crystallization or a chilled-roller flaking, it is possible to obtain compacts that are stable to flaking if these consist predominantly of the thermodynamically stable alpha modification which only melts at 42.5° C.

In view of the cited prior art, the object underlying the present invention was to provide a method for preparing solidified menthol which has the following advantageous properties: the method should be able to be operated as continuously as possible especially on an industrial scale with the lowest possible outlay on apparatus and a high throughput; to provide menthol solidified in one step, where the resulting menthol is obtained in a form that is pourable and only has a slight tendency to cake over a prolonged period, and predominantly in the alpha modification. In addition, the method should be able to be operated particularly economically, i.e. cost-effectively.

DESCRIPTION OF THE INVENTION AND THE PREFERRED EMBODIMENTS

Surprisingly, the object was achieved through the provision of a method for preparing L-menthol in solid form by bringing an L-menthol melt into contact with two chilled surfaces distanced from one another with solidification of the L-menthol melt to give L-menthol in solid form, where the contact between the solidifying L-menthol melt and the chilled surfaces is maintained at least until completion of the solidification.

Suitable starting materials for carrying out the method according to the invention are melts of L-menthol of the formula (I),

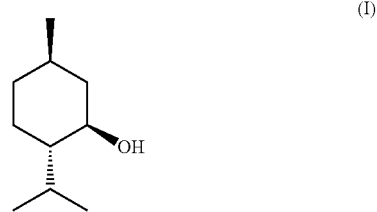

where the molten menthol can be of natural or synthetic origin and has an enantiomer excess of usually at least 95, 96 or 97% ee to 100% ee, preferably 98, 98.5 or 99 to 99.9% ee. Particularly suitable starting materials within the context of the method according to the invention are those melts of L-menthol, which have a content of L-menthol of at least 95, 96 or 97% by weight or above, preferably at least 98 to 100% by weight and very particularly preferably 98, 98.5 or 99 to 99.9% by weight (in each case based on the total weight of the melt), besides impurities such as, for example, remains of solvents, diastereomers of L-menthol of the formula (I) or by-products from synthesis or isolation methods.

Here, the term L-menthol melt is preferably to be understood as meaning L-menthol which is present predominantly, i.e. to at least 80 or better 85% by weight, preferably to at least 90 or 95% by weight and very particularly preferably to at least 95, 96, 97, 98 or 99% by weight in molten form, where the residual weight fractions constitute the amount of solid L-menthol in the melt. Here, the fraction of solid menthol in the melt that is present if appropriate can be that which is still present in the melt as a result of an incompletely concluded melting process of the material used for the provision of the melt, or is added to the completely or partially molten menthol in solid form, for example in the form of crystals of L-menthol in the alpha modification. Such crystals of L-menthol in the alpha modification, which are also referred to as seed crystals, can be obtained, for example in the customary manner by crystallization of L-menthol from an L-menthol-containing solution or melt.

Within the context of a preferred embodiment, those crystals of L-menthol in the alpha modification are used which are obtained by treating the L-menthol melt to be used according to the invention in a scratch chiller, where the seed crystals are formed in situ in the L-menthol melt to be solidified, as a result of which an additional processing step is avoided. Such scratch chillers are known to the person skilled in the art and described, for example, in G. Arkenbout, Melt Crystallization Technology, Technomic Publishing Co. 1995, p. 230.

The L-menthol melt to be solidified is, if desired, usually treated with the smallest possible amounts of said seed crystals of L-menthol in the alpha modification, either, as described above, by adding the crystals to the melt or by generating the crystals in the melt. Usually, the melt to be used is, if desired, treated with said seed crystals in an amount of from 0.1 to 10% by weight, particularly preferably in an amount of from 0.1 to 5% by weight, very particularly preferably in an amount of from 0.1 to 2% by weight, in particular in an amount of from 0.1 to 1% by weight (in each case based on the total amount of the mixture of melt and seed crystals to be used).

Within the context of the method according to the invention, the L-menthol melt to be used according to the invention is usually used at a temperature in the range from about 40 to 60° C., preferably about 43 to 50° C. In this connection, the L-menthol melts in the temperature range below 42 to 43° C., i.e. below the melting point of L-menthol, are supercooled melts.

According to the invention, the L-menthol melt used is brought into contact with two chilled surfaces distanced from one another. Preferably, the L-menthol melt used is located in the interspace between the two distanced, chilled surfaces. The melt can be brought into contact with the individual surfaces simultaneously, i.e. at the same time, or at different times. Usually, as a consequence of processing requirements, the L-menthol melt used is brought into contact with the two chilled surfaces at different times such that the melt comes into contact firstly with one chilled surface and, a short time afterwards, additionally comes into contact with the second chilled surface. In this connection, it has proven to be advantageous to keep the time interval between bringing the L-menthol melt into contact with each of the chilled surfaces as short as possible so that, depending on the temperature difference between the L-menthol melt used and the chilled surface brought into contact first, no extensive or complete solidification of the L-menthol melt used has taken place before contact with the second chilled surface is established. Usually, the time interval between bringing the L-menthol melt used into contact with the respective surfaces is not more than 30 s, preferably up to 20 s and particularly preferably up to 10 s.

Within the context of a preferred embodiment of the method according to the invention, the chilled surfaces to be used according to the invention are in each case smooth surfaces, preferably level sections of continuous belts manufactured from steel, other metals, plastics or combinations of these materials. Particular preference is given to continuous belts made of smooth or polished stainless steel.

The duration of the contact of the melt used, or of the solidifying melt with the two chilled surfaces, referred to below as contact time, can also be the same or different in length for the individual surfaces. Usually the length of the contact time of the melt with the respective chilled surfaces is different since, as explained above, the contacting often takes place at different times and usually also the end of the contact time, i.e. the end of the contact of the completely solidified L-menthol melt with the respective chilled surface, takes place at different times. Irrespective of the sequence of bringing the melt into contact with each of the two chilled surfaces and the detachment of the completely solidified L-menthol melt from the surfaces, the contact times overlap as regards the individual chilled surfaces in terms of time such that the L-menthol melt used and/or the solidifying L-menthol melt is simultaneously in contact with both chilled surfaces over a selectable period of time.

According to the invention, the contact between the solidifying L-menthol melt and the chilled surfaces is maintained at least until completion of the solidification. Within the scope of the present invention, the solidification or crystallization of the L-menthol melt used is preferably only considered to be completed when the resulting L-menthol is present in solid form to at least about 80% by weight or better 85 to 100% by weight, preferably to 90 to 100% by weight, preferably to 95 or 97 to 99.5% by weight and very particularly preferably to 98 to 99% by weight in the alpha modification. L-menthol of this type has only to a small extent changes resulting from conversion of the material to the thermodynamically stabilized modification and therefore changes only to a slight extent, if at all, with regard to its surface nature. The modification of the resulting solidified L-menthol present in each case and thus the completion of the solidification process can be ascertained using methods known to the person skilled in the art, such as X-ray diffraction or powder diffractometry (see e.g. Joel Bernstein, Polymorphism in Molecular Crystals, Oxford University Press 2002, pp. 94-150).

Within the context of the present invention, the term "chilled surfaces" is to be understood as meaning those surfaces which have a temperature below the melting point or solidification point of L-menthol of 42 to 43° C. or are heat-treated to such a temperature. The chilled surfaces to be used according to the invention, independently of one another, usually each have a temperature in the range from about 0 to about 40° C., preferably from about 0 to about 35° C., particularly preferably 5 to 30° C. and very particularly preferably in the range from 10 to 25° C. In this connection, both surfaces can have the same temperature or a different temperature. It is also possible to change, i.e. raise or lower, the temperature of the chilled surfaces, if desired individually, in the course of the particular contact time.

Within the context of a preferred embodiment of the method according to the invention, the two chilled surfaces have a plane-parallel orientation with a distance of usually about 0.2 to 3 mm, preferably 0.3 to 3 mm, particularly preferably 0.5 to 2.5 mm and very particularly preferably from 0.75 to 2.0 mm relative to one another. Here, the term plane-parallel orientation is to be understood as meaning that the two chilled surfaces have the same distance, within the scope of customary measurement accuracies, over the entire region or section brought into contact with the L-menthol melt to be solidified. The interspace formed between the two chilled surfaces is advantageously completely filled with L-menthol since this ensures the largest possible contact area between the chilled surfaces and the L-menthol melt to be solidified.

Depending on the selected temperatures of the L-menthol melt used, and also on the two chilled surfaces, the contact time of the solidifying L-menthol melt with the two chilled surfaces is advantageously chosen so that it only slightly exceeds the duration for the formation of the alpha modification of the solidified L-menthol from the modifications probably formed primarily in the course of the method according to the invention, such as, for example, the gamma modification. Usually the solidification is completed, i.e. the resulting L-menthol is present in solid form as described above to at least 80% by weight in the alpha modification after a contact time of from about 10 to about 300 s, preferably about 20 to about 250 s, preferably to about 200 s and very particularly preferably from 30 to 150 s, preferably to 100 s. In this connection, the specified contact times are to be understood such that they give the time intervals during which there is simultaneous contact between the L-menthol melt and the solidifying or already solidified L-menthol melt at both chilled surfaces. If desired, the contact of the solidified L-menthol melt with one of the two chilled surfaces can, moreover, also be extended.

Within the context of a preferred embodiment of the method according to the invention, short contact times and complete solidification in the alpha modification can be achieved by treating the melt with seed crystals as described above before or during contacting with the chilled surfaces or before or during placement on to the chilling belt. This can be achieved, for example, by stirring into a receiving vessel or scattering precomminuted crystals of the alpha modification of L-menthol on to the L-menthol melt used (the liquid crystal film). In one preferred embodiment of the invention, the seeding is achieved by passing the melt through a heat exchanger operated below the melting point, the walls of which are freed from crystallized-on material by a rubbing element. This arrangement is familiar to the person skilled in the art, for example, in the form of a scratch chiller as specified above. Accordingly, one preferred embodiment of the method according to the invention is one in which the seed crystals are formed by treating the L-menthol melt to be used in a scratch chiller.

The L-menthol in solid form obtained according to the invention can then be removed from the chilled surface or surfaces by methods known to the person skilled in the art. According to the invention, preference is given to removing the solidified L-menthol using an obliquely slanted knife from one or both of the chilled surfaces to give L-menthol in the form of solid flakes.

Within the context of a particularly preferred embodiment, the method according to the invention is carried out using a twin-belt chiller. Twin-belt chillers are known to the person skilled in the art and can be acquired, for example, from Sandvik Process Systems GmbH, D-70736 Fellbach or Kaiser Steelbelt Systems GmbH, D-47800 Krefeld.

When using said twin-belt chillers, the chilled surfaces to be used according to the invention are realized in the form of two continuous belts (chilling belts) usually manufactured from steel and passed in counter-rotation over rollers (see C.M. van't Land, Industrial Crystallization of Melts, Marcel Dekker 2005, p. 63). The solidification of the L-menthol melt according to the invention to give L-menthol in solid form then takes place in the interspace between the plane-parallel sections of the two chilling belts of the twin-belt chiller that face one another.

In order to achieve as simultaneous a contacting of the L-menthol melt to be solidified with the two chilling belts as possible, it is advisable to bring the melt into contact with the chilling belts as close as possible to the point at which the interspace between the plane-parallel sections of the two chilling belts starts, such that premature solidification of the L-menthol melt results to the lowest possible extent.

Following removal of the resulting L-menthol in solid form as described above, preferably by flaking, the material obtained in this way can also be aftertreated by further cooling, for example on a chilled conveying screw or a chilled conveyer belt.

The method according to the invention can be carried out discontinuously, for example, using chilled punches or continuously for example using a twin-belt chiller as specified above. Here, in particular the continuous method has economic advantages.

Through the method according to the invention, L-menthol is available in solid form which, as a result of the solidification in contact with two chilled surfaces, has at least two smooth surfaces, where subsequent conversion of the L-menthol located on the surface from the gamma modification to the alpha modification no longer results on the two surfaces. As a result, the smooth surface structure is retained on the two contact areas to the chilled surfaces which impart to the L-menthol in solid form obtained in this way advantageous properties such as, for example, a smooth, stable surface and a low adhesion tendency, with the specified material properties even being retained after a prolonged storage period of several weeks at ambient temperature. The two smooth surfaces of the solidified menthol obtained according to the invention do not have a tendency to form microscopic needle-shaped crystals growing out of the surface and/or thereon by desublimation which are possibly responsible for the agglomeration tendency of the L-menthol solidified in the conventional manner. Accordingly, in a further aspect, the present invention relates to L-menthol in solid form which is obtainable by the method according to the invention described above.

Dissolving the L-menthol obtainable according to the invention in the form of solid flakes from one or both of the chilled surfaces, preferably the chilling belts of a twin-belt chiller to be used with preference according to the invention, gives semi-transparent L-menthol flakes which have the described advantageous material properties.

Preferably menthol obtainable by the method according to the invention in solidified form or in the form of flakes has, depending on the selected distance between the two chilled surfaces, a uniform thickness of from 0.2 to 3 mm, preferably 0.3 to 3 mm, particularly preferably 0.5 to 2.5 mm, and very particularly preferably 0.75 to 2 mm. The average diameter, based on the smooth surface, can be freely chosen depending on the type of flaking or detachment from the chilled surfaces and ranges from continuous belts to highly comminuted flakes. With regard to ease of handling of the resulting solidified menthol, flakes with an average diameter of from about 1 to about 20 mm, preferably about 3 to about 10 mm, have proven advantageous and are thus preferred according to the invention.

The L-menthol accessible in this way in solid form, in particular that in the form of flakes, is suitable, on account of its advantageous material properties, for further processing, for example for incorporation into utility or consumer goods, such as, for example, pharmaceutical or cosmetic preparations, foods, hygiene or cleaning articles, confectionery or tobacco products. In a further aspect, the present invention therefore relates to the use of the L-menthol obtainable according to the invention in solid form for the production of or incorporation into products such as utility or consumer goods.

The examples below serve to illustrate the invention without limiting it in any way:

Example 1

One drop of molten L-menthol was placed on to a steel plate cooled to 25° C. A steel punch, heat-treated to 25° C., was impressed, with a force of about 2 N/cm², upon the pool of runny menthol which forms prior to complete solidification. The L-menthol solidified within 1 minute to give a wax-like mass and after 2 to 3 minutes had crystallized to the extent that it could be lifted up from the plate with breakage. This gave semi-transparent flakes that were shiny-smooth on both sides.

Example 2

A melt of L-menthol heat-treated to 50° C. was introduced into a scratch chiller heat-treated to 10° C., and discharged in the liquid form, but clouded by seed crystals, and applied via a weir as liquid film to a twin chilling belt heat-treated from both sides to 10° C. After a run time of 90 s at the end of the belt, a 1.5 mm-thick, through-crystallized film of L-menthol was obtained, which was comminuted into flakes 4 to 8 mm in size using a cutter. This gave semi-transparent flakes which appeared shiny on both sides, the pile of which could still be loosened by gentle shaking even after storage for 7 days at temperatures of 25° C. The walls of the storage vessels used exhibited only traces of sublimate deposition.

Comparative Example 1

A melt of menthol heat-treated to 50° C. was fed to the immersion bowl of a flaking roller. A film of L-menthol was drawn on to the roller heat-treated to 15° C., said film solidifying while the roller rotates through the air space. After a residence time of 60 s, a 0.7 mm-thick, still wax-like menthol layer was obtained which, after cooling for a further 2 minutes in the air, was comminuted into flakes 5 to 10 mm in size using a cutter. These flakes had a highly porous, rough surface on one side. After just a few days under ambient conditions their pile was heavily agglomerated, the vessel walls were covered with large amounts of sublimate.

Comparative Example 2

One drop of molten L-menthol was placed on to a steel plate cooled to 25° C. The pool of runny menthol which forms solidified within 2 minutes to give a wax-like mass and, after 3 to 4 minutes, had crystallized to the extent that it could be lifted off from the plate with breakage. This gave L-menthol flakes which had one exceptionally smooth, shiny side and one snow-white luminous, rough surface.

The invention claimed is:

1. A method for preparing L-menthol in solid form by bringing an L-menthol melt into contact with two chilled surfaces distanced from one another with solidification of the L-menthol melt to give L-menthol in solid form, where the contact between the solidifying L-menthol melt and the chilled surfaces is maintained at least until completion of the solidification and where the two chilled surfaces have a plane-parallel orientation with a distance of 0.2 to 3 mm relative to one another and, independently of one another each have a temperature in the range from 0 to 35° C.

2. The method according to claim 1, wherein the contact between the solidifying L-menthol melt and the chilled surfaces is maintained until the L-menthol is present in solid form to at least 80% by weight in the alpha modification.

3. The method according to claim 1, wherein the interspace between the two chilled surfaces is completely filled with menthol.

4. The method according to claim 1, wherein the contact time between L-menthol and the chilled surfaces is 10 to 300 s.

5. The method according to claim 1, wherein an L-menthol melt is used which has an enantiomer excess of at least 95% ee and a content of L-menthol of at least 95% by weight, based on the total weight of the melt.

6. The method according to claim 1, wherein an L-menthol melt with a temperature in the range from 40 to 60° C. is used.

7. The method according to claim 1, wherein the L-menthol melt to be used is treated with 0.1 to 10% by weight of seed crystals of L-menthol before being brought into contact with the chilled surfaces.

8. The method according to claim 7, wherein the seed crystals are formed by treating the L-menthol melt to be used in a scratch chiller.

9. The method according to claim 1, wherein the resulting L-menthol is removed in the form of solid flakes from one or both of the chilled surfaces.

10. The method according to claim 1, which is carried out using a twin-belt chiller.

11. The method according to claim 1, wherein the two chilled surfaces are the plane-parallel sections of the chilling belts of a twin-belt chiller.

12. L-menthol in the form of flakes obtainable by the method according to claim 1.

13. L-menthol flakes according to claim 12 with a thickness of from 0.2 to 3 mm.

14. L-menthol flakes according to claim 12 with an average diameter of from 1 to 20 mm.

15. A utility or consumer good comprising the L-menthol of claim 12 in solid form.

* * * * *